United States Patent
Babbs et al.

(10) Patent No.: US 6,475,232 B1
(45) Date of Patent: Nov. 5, 2002

(54) STENT WITH REDUCED THROMBOGENICITY

(75) Inventors: Charles F. Babbs; Neal F. Fearnot; Stephen F. Badylak; Leslie A Geddes, all of West Lafayette; Michael C. Hiles, Lafayette; Joe D. Bourland, West Lafayette, all of IN (US)

(73) Assignee: Purdue Research Foundation, West Lafayette, IN (US)

(*) Notice: Subject to any disclaimer, the term of this patent is extended or adjusted under 35 U.S.C. 154(b) by 0 days.

(21) Appl. No.: 09/319,718
(22) PCT Filed: Dec. 10, 1997
(86) PCT No.: PCT/US97/22586
§ 371 (c)(1), (2), (4) Date: Jun. 10, 1999
(87) PCT Pub. No.: WO98/25544
PCT Pub. Date: Jun. 18, 1998

Related U.S. Application Data

(60) Provisional application No. 60/032,682, filed on Dec. 10, 1996.

(51) Int. Cl.⁷ .................................................. A61F 2/06
(52) U.S. Cl. ........................................................ 623/1.13
(58) Field of Search ............................. 623/1.13, 1.25, 623/1.36, 1.46–1.5; 606/198, 197, 195, 194

(56) References Cited

U.S. PATENT DOCUMENTS

| | | | |
|---|---|---|---|
| 4,902,508 A | * | 2/1990 | Badylak et al. ............... 425/95 |
| 4,986,831 A | | 1/1991 | King et al. |
| 5,122,154 A | * | 6/1992 | Rhodes ....................... 606/198 |
| 5,123,917 A | * | 6/1992 | Lee |
| 5,192,307 A | | 3/1993 | Wall |
| 5,275,826 A | | 1/1994 | Badylak et al. |
| 5,281,422 A | | 1/1994 | Badylak et al. |
| 5,316,023 A | | 5/1994 | Palmaz et al. |
| 5,554,389 A | | 9/1996 | Badylak et al. |
| 5,681,345 A | | 10/1997 | Euteneuer |
| 5,683,453 A | * | 11/1997 | Palmaz |
| 5,693,085 A | * | 12/1997 | Buirge et al. ................. 623/1 |
| 6,165,212 A | * | 12/2000 | Dereume et al. .......... 623/1.13 |

FOREIGN PATENT DOCUMENTS

| | | |
|---|---|---|
| GB | 1195992 | 6/1970 |
| WO | WO 95/29647 | 11/1995 |
| WO | 98/25544 | 6/1998 |
| WO | 98/25636 | 6/1998 |

OTHER PUBLICATIONS

8th Congress of the International Cardivacular Society. Vienna Sep. 6–9, 1967. XP00206303. pp. 235–236.*
8$^{th}$ is Congress of the International Cardiovascular Society. Vienna Sep. 6–9, 1967. XP002062303. pp. 235–236.
"Autologous Vein Graft Coating Applied to Vascular Stents: An Experimental Study" by C. Stefanadis, K.P. Toutouzas, C. Vlachopoulos, I. Kallikazaros, P. Karayannakos, C. Stratos, E. Tsiamis, and P. Toutouzas; Restenosis Summit VI (1994) p. 75.

* cited by examiner

*Primary Examiner*—Michael H. Thaler
(74) *Attorney, Agent, or Firm*—Barnes & Thornburg

(57) ABSTRACT

A tissue graft construct and method for repairing the inner linings of damaged or diseased vertebrate vessels is described. The method comprises the steps of positioning a tissue graft construct within a blood vessel at a site in need of repair. The tissue graft construct comprises a stent (3) covered with submucosal tissue (4) wherein the stent (3) is formed for receiving the distal end of a catheter (1) having an inflatable balloon (2).

4 Claims, 4 Drawing Sheets

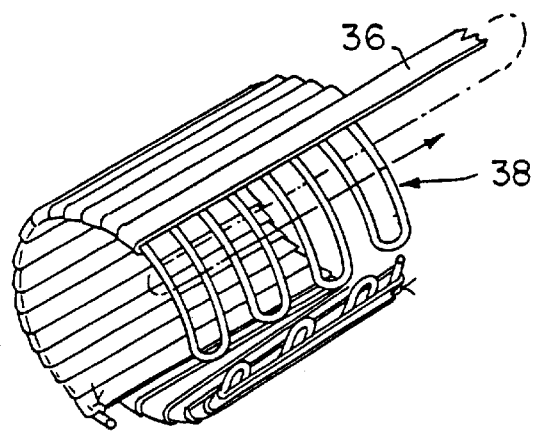
FIG. 3a
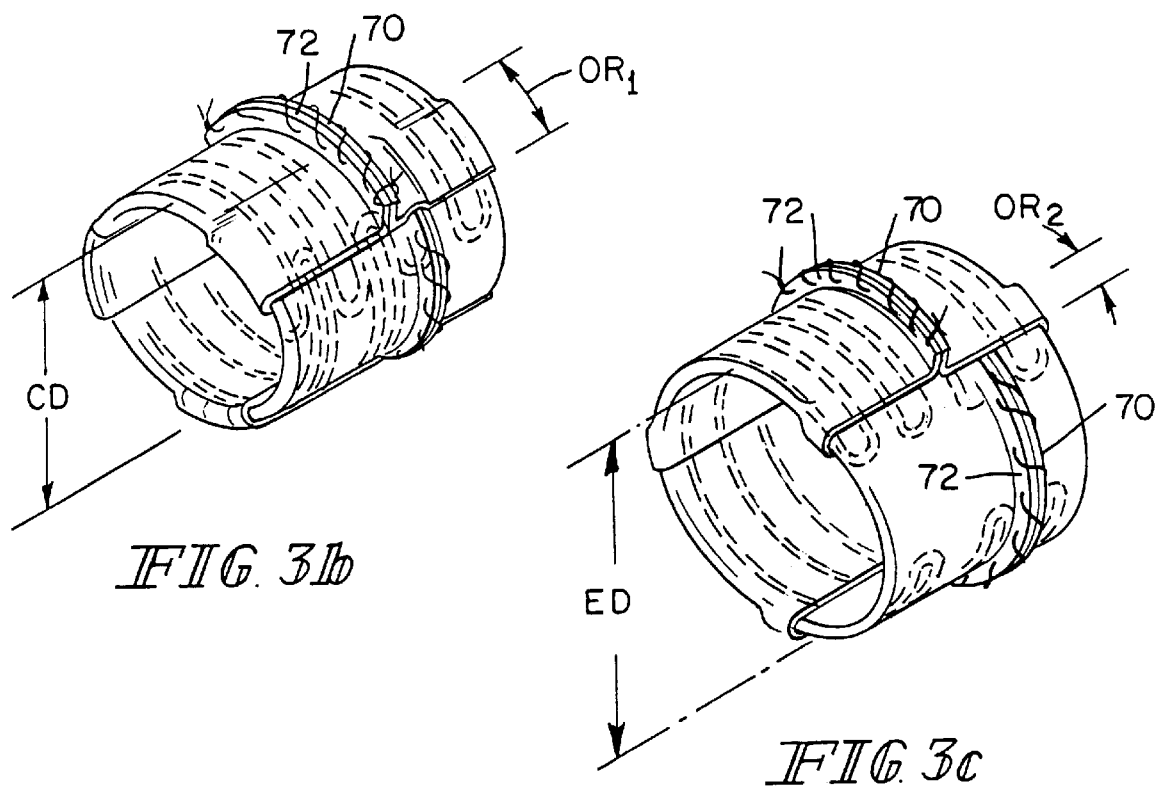
FIG. 3b
FIG. 3c

STENT WITH REDUCED THROMBOGENICITY

CROSS-REFERENCE TO RELATED APPLICATIONS

This application is a U.S. national application of international application Ser. No. PCT/US97/22586 filed Dec. 10, 1997, which claims priority to U.S. provisional application Ser. No. 60/032,682 filed Dec. 10, 1996

FIELD OF THE INVENTION

This invention relates to an intestinal tissue covered prosthesis useful in promoting the resurfacing and repair of damaged or diseased tissue structures. More particularly this invention is directed to stents having a layer of submucosal tissue covering a surface of the stent, and their use in repairing damaged or diseased physiological vessels, particularly blood vessels.

BACKGROUND AND SUMMARY OF THE INVENTION

The most common cause of vascular disease in the Western world is atherosclerosis, in which cholesterol and fibrous tissue, often together with calcium precipitates, gradually build up within the inner layers of the arterial wall, diminishing the cross sectional area available for blood flow. There are two essential abnormalities of such atherosclerotic lesions that cause complications. The first is the narrowing of the lumen, which produces a chronic limitation of blood flow distally. The second is the abnormally raised, roughened inner surface of the artery, the physical properties of which tend to induce platelet adhesion and clot formation at the diseased site. Thrombosis can produce sudden cessation of blood flow with disastrous consequences for downstream organs such as the brain, heart muscle, kidney, or lower extremities. The eroded, abnormal intimal surface of sclerotic vessels causes additional complications including fragmentation of atherosclerotic material with downstream embolization and hemorrhage or dissection of blood into the plaque itself causing sudden expansion of the lesion and occlusion of the vessel.

Percutaneous transluminal angioplasty (PTA), first performed 25 years ago by Dotter and Judkins, is the technique of opening narrowed or occluded blood vessels by passing guide wires and catheters through the stenotic or occluded portion of the blood vessel. Dotter's original PTA method involved inserting increasingly larger catheters over a guidewire to progressively dilate the vessel. Later modifications utilized graduated catheters with gradually tapering tips, which created more lateral compression and less longitudinal shearing action. These early PTA procedures were limited by the requisite stiffness of the catheters and by the large puncture wounds required for the procedure.

In 1974, PTA procedures were revolutionized by the introduction of balloon catheter angioplasty. A balloon catheter has an expandable sac that can be expanded and contracted in a controlled manner in response to inflation pressure. Balloon catheter angioplasty involves positioning the balloon catheter at a stenotic site and inflating the sac to a predetermined size to open the stenotic or occluded portion of the blood vessel. The sac is then deflated and the catheter removed leaving a larger lumen. Standard balloon angioplasty, with or without the use of stents, produces a torn vessel with myointimal flaps and exposed fissures. These provide thrombogenic surfaces and sites for hemodynamic dissection. Furthermore, although the use of the stents in PTA procedures gives highly predictable immediate angiographic results, those stents all suffer the disadvantage that they have limited long term efficacy. Despite holding the vessel open, the natural reparative processes at a stent-dilated vessel result in healing tissues growing around the stent structure and eventually occluding the lumen of the vessel. In addition to PTA procedures, alternative techniques for removing atherosclerotic plaques include laser angioplasty and mechanical arthrectomy devices, which can vaporize, melt, or remove plaque material. However all such systems leave an abnormal, thrombogenic surface.

Angioplasty is now known to damage the vessel wall by tearing and stretching, and this form of controlled injury opens the vessel lumen and increases blood flow acutely in nearly all cases. However, abrupt vessel closure during or immediately following PTA and late restenosis continues to limit the effectiveness of the procedure. To enhance the efficacy of PTA procedures catheters have been fitted with vascular stents.

Stents are three dimensional implantable structures that (upon delivery to an intra vessel position) physically hold a blood vessel open. Vascular stents are typically formed to fit on the end of conventional catheters for delivery of the stent to a predetermined intravascular location. A number of stents for coronary use are commercially available. They differ in physicochemical characteristics and the mode of implantation. Ideally, a stent should be flexible, thrombo-resistant, low in profile, radiopaque, limit the expansion of repair tissues into the lumen of the vessel, and have an easy, reliable delivery system. Currently available expandable stents can be categorized as "self expandable stents" and "balloon expandable stents." Self-expanding stents utilize a spring mechanism to constrain the stent to a compressed shape. Upon removal of the constraint, the stent expands to a predetermined dimension. Balloon expandable stents are expandable members formed to fit over a balloon catheter and capable of being expanded in response to controlled inflation of the balloon catheter. Inflation of the balloon results in plastic deformation of the stent beyond its elastic limits so that the stent remains in its expanded state upon subsequent deflation and removal of the balloon catheter. Preferably stents used in conjunction with PTA are "expandable stents" having an initial collapsed state that allows the stent to be delivered to the desired intravascular location with minimal longitudinal shearing action. Upon delivery to the desired location the stent is expanded to fix the stent at that location and to physically hold the vessel open.

The present invention utilizes a natural collagenous matrix comprising submucosal tissue in combination with known angioplastic techniques to eliminate complications that derive from the residual abnormal, thrombogenic surfaces produced by current available angioplastic techniques such as ordinary balloon angioplasty, laser angioplasty, and transluminal mechanical arthrectomy. The collagenous matrices for use in accordance with the present invention comprise highly conserved collagens, glycoproteins, proteoglycans, and glycosaminoglycans in their natural configuration and natural concentration. One preferred collagenous matrix comprises warm-blooded vertebrate submucosa.

In accordance with the present invention the submucosa is isolated from warm-blooded vertebrate tissues including the alimentary, respiratory, intestinal, urinary or genital tracts of warm-blooded vertebrates. The preparation of intestinal submucosa is described and claimed in U.S. Pat. No. 4,902,508, the disclosure of which is expressly incorporated herein by reference. Urinary bladder submucosa and its preparation is described in U.S. Pat. No. 5,554,389, the disclosure of which is expressly incorporated herein by reference. Stomach submucosa has also been obtained and characterized using similar tissue processing techniques. Such is described in U.S. patent application No. 60/032,683 titled STOMACH SUBMUCOSA DERIVED TISSUE GRAFT, filed on Dec. 10, 1996. Briefly, stomach submucosa is prepared from a segment of stomach in a procedure similar to the preparation of intestinal submucosa. A segment of stomach tissue is first subjected to abrasion using a longitudinal wiping motion to remove the outer layers (particularly the smooth muscle layers) and the luminal portions of the tunica musoca layers. The resulting submucosa tissue has a thickness of about 100 to about 200 micrometers, and consists primarily (greater than 98%) of acellular, eosinophilic staining (H&E stain) extracellular matrix material.

Preferred submucosal tissues for use in accordance with this invention include intestinal submucosa, stomach submucosa, urinary bladder submucosa, and uterine submucosa. Intestinal submucosal tissue is one preferred starting material, and more particularly intestinal submucosa delaminated from both the tunica muscularis and at least the tunica mucosa of warm-blooded vertebrate intestine.

As a tissue graft, submucosal tissue undergoes remodeling and induces the growth of endogenous tissues upon implantation into a host. It has been used successfully in vascular grafts, urinary bladder and hernia repair, replacement and repair of tendons and ligaments, and dermal grafts. The preparation and use of submucosa as a tissue graft composition is described in U.S. Pat. Nos. 4,902,508; 5,281,422; 5,275,826; 5,554,389; and other related U.S. patents. When used in such applications the graft constructs appear not only to serve as a matrix for the regrowth of the tissues replaced by the graft constructs, but also promote or induce such regrowth of endogenous tissue. Common events to this remodeling process include: widespread and very rapid neovascularization, proliferation of granulation mesenchymal cells, biodegradation/resorption of implanted intestinal submucosal tissue material, and lack of immune rejection. The use of submucosal tissue in sheet form and fluidized forms for inducing the formation of endogenous tissues is described and claimed in U.S. Pat. Nos. 5,281,422 and 5,275,826, the disclosures of which are expressly incorporated herein by reference.

The present invention is directed to an improved prosthetic device for repairing the intimal surface of damaged or diseased vessels. The prosthetic devices of the present invention can also be used in traditional PTA procedures to open narrowed or occluded vessels. In one embodiment the prosthetic device comprises a cylindrical shaped expandable member having a luminal and exterior surface, and a layer of submucosal tissue fixed to the exterior or luminal surface of the member. The expandable member is typically a stent wherein expansion of the stent increases the circumference of said member, thus fixing the device at a predetermined location within the vessel.

BRIEF DESCRIPTION OF THE DRAWINGS

FIGS. 3a–3c are perspective views of a stent, wrapped longitudinally with one or more sheets of submucosal tissue.

FIG. 3a illustrates a stent, wrapped longitudinally with a single sheet of submucosal tissue. FIG. 3b and FIG. 3c illustrate a stent wrapped with three separate sheets of submucosal tissue, each sheet forming a single loop of submucosal tissue, wherein the stent is shown in its condensed state (FIG. 3b) or in its expanded state (FIG. 3c).

FIG. 4a shows the tissue in its compact state and FIG. 4b shows the tissue in its expanded state.

FIG. 6a illustrates a stent wire covered with a narrow sheet of submucosal tissue and FIG. 6b and FIG. 6c illustrate a stent formed from the submucosa tissue covered wire of FIG. 6a.

DETAILED DESCRIPTION OF THE INVENTION

Figure 1:
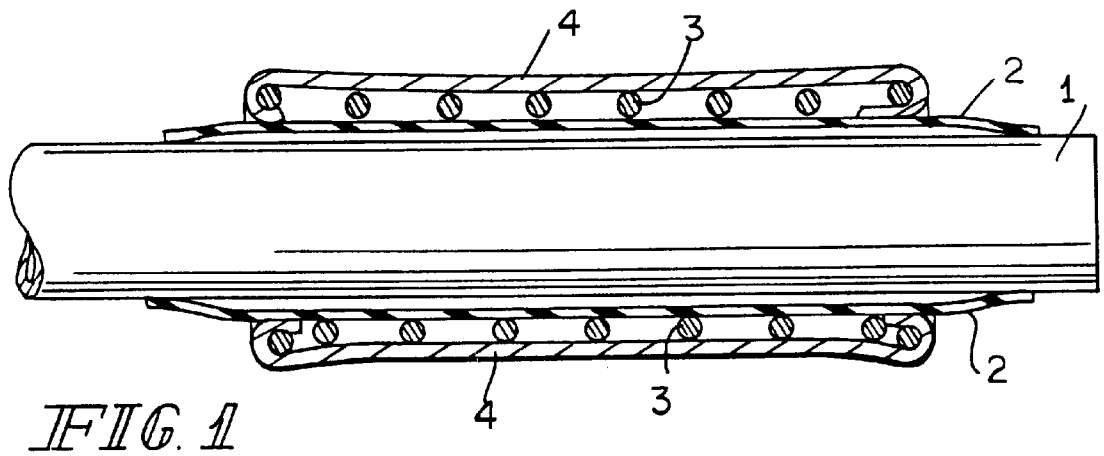
FIG. 1 is a cross-sectional view of a balloon catheter carrying a submucosa tissue coated stent in accordance with this invention.

The present invention is directed to an improved vascular stent composition and a method for repairing the inner linings of damaged or diseased vessels. The method comprises the step of applying a new, non-thrombogenic intimal surface of submucosal tissue over the former damaged or diseased intima. The term "vessel" as used herein is defined as including any bodily canal, conduit, duct or passageway, including but not limited to blood vessels, bile ducts, the esophagus, the trachea, the ureter and the urethra. In one embodiment the vessel is expanded to increase the lumen of the vessel simultaneously with the application of a layer of submucosal tissue. Applicants have discovered that the applied submucosal tissue layer provides a non-thrombogenic surface that induces the formation of a new endothelium and inhibits restenosis of a vessel after expansion of the vessel.

Submucosal tissue suitable for use in the present invention comprises naturally associated extracellular matrix proteins, glycoproteins, proteoglycans, glycosaminoglycans and other factors in their natural configuration and natural concentration. Submucosal tissue can be prepared from a variety of natural sources including the alimentary, respiratory, intestinal, urinary or genital tracts of warm-blooded vertebrates.

In one embodiment of the present invention the submucosal tissue comprises intestinal submucosa delaminated from both the tunica muscularis and at least the luminal portion of the tunica mucosa. In another embodiment the intestinal submucosal tissue comprises the tunica submucosa and basilar portions of the tunica mucosa including the lamina muscularis mucosa and the stratum compactum which layers are known to vary in thickness and in definition dependent on the source vertebrate species.

The preparation of intestinal submucosal tissue for use in accordance with this invention is described in U.S. Pat. No. 4,902,508. A segment of vertebrate intestine, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. One preferred source of intestinal submucosa is the small intestine of mature adult pigs weighing greater than 450 lbs. The submucosal tissue is rinsed several times with saline and optionally sterilized.

The submucosal tissue of the present invention can be sterilized using conventional sterilization techniques including glutaraldehyde tanning, formaldehyde tanning at acidic pH, propylene oxide treatment, gas plasma sterilization, gamma radiation, electron beam radiation, and peracetic acid sterilization. Sterilization techniques which do not adversely affect the mechanical strength, structure, and biotropic properties of the submucosal tissue are preferred. For instance, strong gamma radiation may cause loss of strength of the sheets of submucosal tissue. Preferred sterilization techniques include exposing the graft to peracetic acid, 1–4 Mrads gamma irradiation (more preferably 1–2.5 Mrads of gamma irradiation) or gas plasma sterilization; peracetic acid sterilization is the most preferred sterilization method.

Submucosal tissue treated with peracetic acid exhibits little if any significant post-implantation calcification. The treatment is typically conducted at a pH of about 2 to about 5 in an aqueous ethanolic solution (about 2 to about 10% ethanol by volume) at a peracid concentration of about 0.03 to about 0.5% by volume. Typically, the submucosal tissue is subjected to two or more sterilization processes. After the submucosal tissue is sterilized, for example by chemical treatment, the tissue may be wrapped in a plastic or foil wrap and sterilized again using electron beam or gamma irradiation sterilization techniques.

The submucosal tissue specified for use in accordance with this invention can also be in a fluidized form. The preparation of fluidized forms of submucosa tissue is described in U.S. Pat. No. 5,275,826, the disclosure of which is expressly incorporating herein by reference. Fluidized forms of submucosal tissue are prepared by comminuting submucosa tissue by tearing, cutting, grinding, or shearing the harvested submucosal tissue. Thus pieces of submucosal tissue can be comminuted by shearing in a high speed blender, or by grinding the submucosa in a frozen or freeze-dried state to produce a powder that can thereafter be hydrated with water or a buffered saline to form a submucosal fluid of liquid, gel or paste-like consistency.

The comminuted submucosa formulation can further be treated with an enzymatic composition to provide a homogenous solution of partially solubilized submucosa. The enzymatic composition may comprise one or more enzymes that are capable of breaking the covalent bonds of the structural components of the submucosal tissue. For example, the comminuted submucosal tissue can be treated with a collagenase, glycosaminoglycanase, or a protease, such as trypsin or pepsin at an acidic pH, for a period of time sufficient to solubilize all or a major portion of the submucosal tissue protein components. After treating the comminuted submucosa formulation with the enzymatic composition, the tissue is optionally filtered to provide a homogenous solution.

The viscosity of fluidized submucosa for use in accordance with this invention can be manipulated by controlling the concentration of the submucosa component and the degree of hydration. The viscosity can be adjusted to a range of about 2 to about 300,000 cps at 25° C. Higher viscosity formulations, for example, gels, can be prepared from the submucosa digest solutions by adjusting the pH of such solutions to about 6.0 to about 7.0.

Submucosal tissue can be stored in a hydrated or dehydrated state. Lyophilized or air dried submucosa tissue can be rehydrated and used in accordance with this invention without significant loss of its biotropic and mechanical properties.

Submucosal tissue can be used in accordance with the present invention in combination with standard PTA devices to form prosthetic devices suitable for use in PTA procedures. Applicants anticipate that the use of the present tissue graft constructs comprising submucosal tissue will enhance the repair of damaged or diseased vessels and thus improve the effectiveness of PTA procedures. The method of repairing vessels in vivo through the use of the disclosed devices comprises the steps of contacting the intima surface of the vessel with submucosal tissue and holding the submucosal tissue in place to provide a new intimal surface. Advantageously, the implanted layer of submucosal tissue induces the growth of new endothelium without stenosis, and therefore the submucosal tissue is preferably held in contact with the site in need of repair for a time sufficient to induce the formation of a new intimal surface. In preferred embodiments the tissue graft construct is permanently located within a blood vessel or other structure and is ultimately replaced by endogenous cell growth.

In one embodiment of the present invention submucosal tissue is used in combination with known angioplastic techniques and devices to provide an improved composition and method for repairing damaged or diseased portions of vessels. The improvement method comprises fixing a graft construct comprising submucosal tissue onto the surface of a catheter and delivering the tissue graft construct to a predetermined intra-vessel location. It is anticipated that the vessel walls of any bodily vessel, conduit, canal or body cavity that is accessible to a catheter, can be repaired using the method described in the present invention.

Conventional catheters can be used to position the submucosal graft constructs to an intra-vessel location for contact with a diseased or damaged surface of the vessel. In accordance with one embodiment, the catheter is a balloon catheter, and the balloon portion is covered with submucosal tissue. Upon positioning of the submucosal tissue covered catheter within a vessel, inflation of the balloon presses the submucosal tissue against the intimal surface of the vessel. Subsequent deflation of the balloon portion allows the removal of the catheter, leaving the submucosal tissue positioned in contact with the intimal surface of the vessel.

The submucosal tissue is preferably combined with additional elements to enhance the retention of the submucosal tissue layer on the original intima surface including, use of anchoring projections (such as plastic or metal pins), adhesives, stents, or other fixation devices known to those skilled in the art. In preferred embodiments the submucosal tissue is held in contact with the intimal surface through the use of a stent.

In accordance with one embodiment an improved stent is provided for opening obstructed or occluded vessels. The improved stent comprises a conventional expandable stent, wherein the exterior surface of the stent is covered with submucosal tissue. Upon deployment of the submucosal tissue covered stent, the submucosal tissue covers the original intima surface of the vessel to provide a smooth, non-thrombogenic surface. For example, in one embodiment the exterior surface of a stent is covered with submucosal tissue and a catheter is used to position the stent to a predetermined location in a blood vessel. The stent is expanded, and thereby expands the lumen of the vessel, and the submucosal tissue is pressed against the luminal surface of the vessel thus covering the arteriosclerotic lesions and the surface of blood vessels damaged through the angioplasty procedure.

Table 1 provides a list of several stents suitable for use in accordance with the present invention, however the list is not exhaustive and additional stents known to those skilled in the art can be used in accordance with the present invention.

TABLE 1

Design and Characteristics of Stents in Clinical Evaluation

| Stent | Configuration | Filament Composition | Filament Thickness (mm) | Stent Diameter (mm) | Stent Length (mm) | Surface Area (%) | Radiopaque* |
|---|---|---|---|---|---|---|---|
| Self-expanding | | | | | | | |
| Wallset | Wire-mesh | Stainless Steel | 0.07–0.10 | 3.5–6.0 | 21–45 | 15.5–20 | No |
| Balloon-expandable | | | | | | | |
| Palmaz-Schatz | Slotted tube | Stainless Steel | 0.08 | 3.0–4.0 | 15 | 10 | No |
| Gianturco-Roubin | Incomplete coil | Stainless Steel | 0.15 | 2.0–4.0 | 20 | 10 | No |
| Wiktok | Helical coil | Tantalum | 0.125 | 3.0–4.0 | 15–17 | 5–10 | Yes |
| Streker | Woven wire | Stainless steel/ tantalum | 0.07 | 2.0–3.5 | 15–25 | — | No Yes |

In one embodiment, a prosthetic device utilizing a stent incorporates a conventional balloon angioplasty catheter around which are placed, in order, an expandable vascular stent, and a layer of submucosal tissue. Alternatively the stent can be sandwiched between two layers of submucosal tissue (i.e., one layer covering the luminal surface of the stent and one layer covering the external surface of the stent). The submucosal tissue is immobilized onto the stent through the use of adhesives, sutures, interweaving the tissue with the stent struts or other fixation techniques known to those skilled in the art.

The graft constructs of the present invention can be utilized in combination with conventional prosthetic devices known to those skilled in the art as being useful for vessel repair. For example the submucosal tissue constructs of the present invention are fixed onto the distal end of a prosthetic device, such as a catheter, using a variety of techniques including: frictional engagement, applying the tissue onto the surface of the prosthetic device followed by drying the material, suturing the tissue to the device, and other means known to those skilled in the art.

In one preferred embodiment, the graft construct comprises an expandable cylindrical shaped member that has submucosal tissue covering at least the external surface of the member. In this embodiment the lumen of the cylindrical member is sized for receiving the distal end of a catheter, and more preferably the expandable member is formed to frictionally engage the exterior surface of the distal end of the catheter. The expansion of the expandable member increases the circumference of the cylindrical shaped member thus fixing the submucosal tissue against the luminal surface of the vessel and allowing for the removal of the catheter after deployment of the graft construct.

In one embodiment the catheter comprises a balloon-type catheter and the expandable member comprises a stent that is expanded to a fixed enlarged size by the inflation of the balloon catheter. In this embodiment, inflation of the submucosal tissue/stent-covered balloon catheter accomplishes several therapeutic objectives, almost simultaneously. First, as in conventional balloon angioplasty, the lumen is forcibly dilated to reverse narrowing caused by an atherosclerotic plaque. Second, the vascular stent maintains the expanded caliber of the vessel, providing a degree of rigid support and maintaining a circular, isodiametric cross-sectional profile. In addition the stent, in combination with intra-arterial pressure, holds the submucosal tissue against the intima surface of the vessel covering any cracks, fissures, or tears in the vessel that result during balloon inflation. Such defects in blood vessels are highly thrombogenic when exposed to the blood stream. The new submucosal tissue also provides a barrier between the metallic stent and vascular smooth muscle, inhibiting late re-stenosis. Finally, the submucosal tissue layer covers the old, diseased inner lining of the vessel (tunica intima), substituting a smooth, non-thrombogenic surface, into which healthy new endothelial cells can grow, ultimately replacing the submucosal tissue with new endothelium.

Commercially available stents that are best suited for use in accordance with the present invention are metallic (typically stainless steel or tantalum) and are carried in a collapsed form over a conventional balloon angioplasty catheter. When the balloon is inflated the stent is deployed and expanded to its working, in vivo size. However, other types of stents, such as self-expanding stents, can also be used in accordance with the present invention to resurface damaged or diseased body vessels.

One submucosal tissue covered stent construct suitable for use in the present invention comprises a stent having one or more pieces of submucosal covering the exposed external surfaces of the stent. Upon implantation into a host the submucosal tissue is held between the stent and the diseased vessel wall. In one preferred embodiment the stent is positioned to the desired location in the vessel through the use of a balloon-type catheter. In this embodiment shown in FIG. 1, a single lumen angioplasty catheter 1 having an inflatable balloon 2, which is semi-rigid or rigid upon inflation, carries a vascular stent 3 covered with small intestinal submucosa 4. This embodiment of the invention is intended for segments of vessels without significant side branches, such as the renal arteries, the common carotid arteries, or the popliteal arteries. Because of the absence of significant side branches, the lack of perforations in the submucosal tissue will not pose problems for tissue perfusion.

Figure 2:
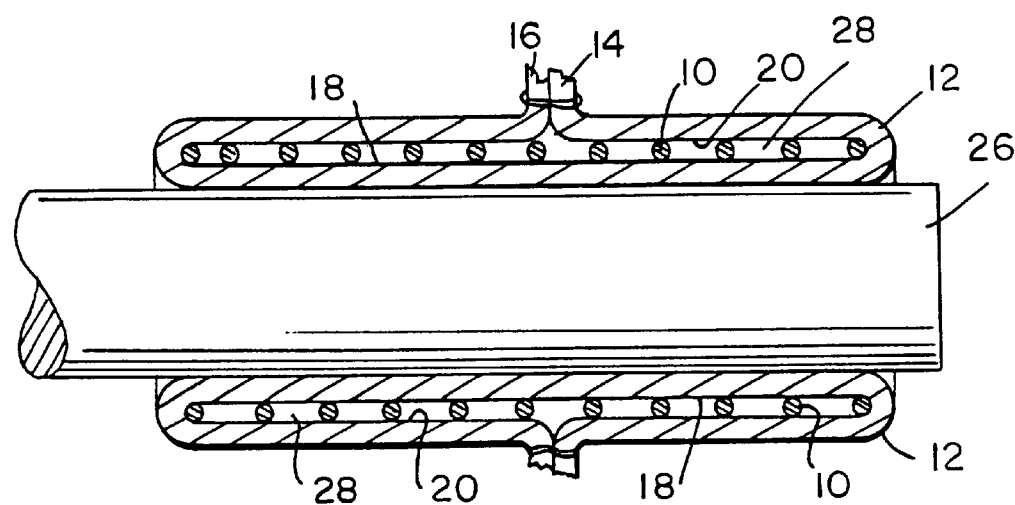
FIG. 2 is a sectional view of a submucosa covered stent positioned on a mandrel.

In another embodiment (FIG. 2) the submucosal tissue 12 overlays both the luminal surface 18 and the exterior surface 20 of the stent 10 to covered all stent surfaces with submucosal tissue 12. Such a submucosal tissue covered stent is prepared in accordance with one embodiment by first preparing a tubular submucosal tissue construct, longer than the stent (preferably twice as long as the stent). A mandrel 26 of the appropriate size is inserted into the lumen of a tube of submucosal tissue and the stent 10 is then fashioned around the submucosal tissue 12. The leading edge 14 and the trailing edge 16 of submucosal tissue 12 are inverted, brought back over the exterior surface 20 of the stent 10 and sutured together, as shown in cross-section in FIG. 2. In this embodiment, wherein both the luminal inward and exterior 20 surfaces of the stent are covered with submucosal tissue, a lumen 28 is formed between the outer and inner layers of the submucosal tissue. The lumen 28 can optionally be filled with fluidized submucosal tissue, growth factors, a heparin containing composition or other components to assist the repair of the damaged or diseased vessel.

The tube of submucosal tissue used to prepare the submucosa covered stents of the present invention can be prepared in accordance with procedures described in U.S. Pat. No. 5,902,508. In one embodiment a tube of submucosa tissue is prepared from intestinal submucosa that has been delaminated from both the tunica muscularis and at lest the luminal portion of the tunica mucosa. The appropriate sized lumen of the tube of submucosa can be prepared by inserting a glass rod/mandrel, having the appropriate diameter, into the lumen of the tube of submucosa and gathering up the redundant tissue and suturing longitudinally along the gathered material.

Alternatively, a sheet of submucosa can be used to form the tube of submucosal tissue. In one embodiment the sheet of submucosal tissue is rolled up around the distal end of the catheter and the opposing lateral ends are situated to form a tube that frictionally engages the catheter. Alternatively the graft construct can be formed to define a tube of submucosa having a diameter approximately the same as the catheter by wrapping the submucosal tissue around an appropriately sized mandrel. The formed tube of submucosal tissue can then be fixed onto the distal end of a catheter. The tube of submucosal tissue is held in its cylindrical shape by sutures, adhesives, compressing the tissue under dehydration conditions, heat treating the tissue, the use of crosslinking agents or any combination thereof. In one embodiment multiple strips of submucosal tissue are overlapped with one another as they are wrapped onto the mandrel to form a multi-layered tube of submucosal tissue. In accordance with the present invention the submucosal tissue can be wrapped onto the mandrel in a variety of different orientations, provided that no gaps exist between the seams of overlapped tissue that would expose the surface of the mandrel.

In one embodiment a submucosal tissue covered stent construct is formed by wrapping the stent with one or more strips of submucosal to cover both the luminal and the exterior surfaces of the stent. For example, a single long narrow sheet of submucosal tissue 36 can be wrapped longitudinally along the exterior surface of the stent 38 starting at one end of the stent, running along the exterior surface to the second end of the stent and then running along the luminal surface, from the second end back to the first end (See FIG. 3a). The longitudinal wrapping is continued forming continuous loops of submucosal tissue that cover the luminal and exterior surfaces of the stent 38. In one preferred embodiment the strip of submucosal tissue is wrapped longitudinally so that each loop overlaps with the previously underlying strip. The overlapped region may range from about 20% up to about 75%. The width of the individual strips and the amount of overlap will vary according to the size and type of stent selected. In addition, the stent can optionally be covered with additional strips of submucosal tissue to increase the thickness of the submucosal layer. The appropriate parameters (width of the sheet of submucosal tissue and percent overlap) will be selected to ensure that upon deployment of the stent 38 the stent surface will not become exposed. Accordingly, upon expansion of the circumference of the stent the individual loops of overlapped submucosal tissue will slide over one another to allow for the increased size of the stent without exposing the surface of the stent.

In one embodiment the luminal and exterior surfaces are covered by a single strip of submucosal tissue, wherein the strip of submucosal tissue has a width less than the circumference of the stent. The strip of submucosal tissue is longitudinally wrapped about the exterior and luminal surfaces to form loops of submucosal tissue that cover the entire surface of the stent. Preferably the loops of submucosal tissue will overlap with each other to such an extent that the stent can be expanded to its in vivo working size without exposing the surface of the stent.

In another embodiment (FIG. 3b) both the luminal surface an the exterior surface of the stent are covered by a plurality of separate sheets of submucosal tissue, each of which are wrapped longitudinally about the exterior and luminal surface of the stent to form loops of submucosal tissue. As shown in FIGS. 3b and 3c three sheets of submucosal tissue each having a first end 70 and a second end 72 are longitudinally wrapped around the luminal and exterior surface of the stent and the first and second ends (70 and 72, respectively) are sutured together to form 3 separate loops of submucosal tissue. In the collapsed form shown in FIG. 3b the stent has a collapsed luminal diameter CD and the three sheets of submucosal tissue overlap one another by an overlap region, $OR_1$. When the stent is deployed the diameter of the stent lumen is expanded to a second diameter, ED, wherein ED is greater than CD. (See FIG. 3c). The sheets of submucosa slide past one another to account for the increase in the circumference of the expanded stent and the overlapped region decreases in size to a distance $OR_2$ wherein $OR_1$ is greater than $OR_2$. Hence, both the inward and outward facing surfaces of the stent remain covered with submucosal tissue, and both the blood and underlying vascular wall "see" only submucosal tissue. Alternatively in one embodiment the individual loops of submucosal tissue shown in FIG. 3b and FIG. 3c cover only the exterior surface of the stent, and the two opposite ends of each sheet of submucosal tissue are looped around the first and second end coil, respectively, of the stent and sutured.

Figures 4A, 4B:
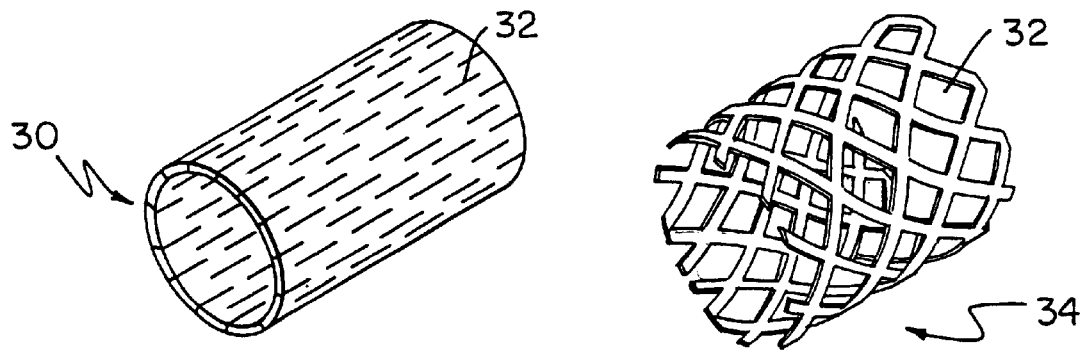
FIGS. 4a and 4b are perspective views of a tube of a submucosa having a plurality of longitudinal slits formed in the walls of the tube.

Applications involving the repair of vessels that have several branches (such as the left anterior descending coronary artery, that has several smaller, but metabolically significant side branches) requires modification of the basic device. In accordance with FIGS. 4a and 4b, a sleeve of submucosal tissue 30 is placed over a stent, and the tissue covered stent is placed over an angioplasty balloon. Staggered rows of longitudinal slits 32 are cut in the submucosal tissue, as shown in FIG. 4a. When the balloon-stent unit is expanded, the submucosal tissue opens to form a submucosal tissue mesh 34, through which blood can pass from the central lumen into side branches (FIG. 4b).

The mesh provides a matrix for in growth of native endothelial tissue, however high blood flow rates through the open spaces in the mesh where vessel side branches exist will tend to retard thrombosis, maintaining the opening in the submucosal mesh. Occasional obstruction of a side branch by the substance of the mesh can occur, but by optimizing mesh size, blood flow to the side branches will be preserved.

Attachment of the slit submucosal tissue to the coils of the underlying stent is accomplished by the placement of sutures through adjacent slits in the tissue and around individual stent coils to form gathers of submucosal tissues. As the balloon stent complex is expanded in vivo, the meshwork opens to the pre-planned final diameter, and the gathers are drawn taut.

Alternatively, a slitted tube of submucosal tissue can be used to cover both the exterior and luminal surface of the stent to repair vessels that have several branches. In this embodiment, a slitted sheet of tubular submucosal tissue, twice as long as the stent, is laid down over the surface of a mandrel, and a stent is fashioned around it. Then the leading and trailing edges of slitted submucosal tissue are everted, brought back over the exterior surface of the stent and sutured together to secure the submucosal tissue around both the blood-facing and tissue-facing surfaces of the stent. In this case suturing the submucosal tissue to the individual coils of the stent is not necessary, the single suture line is sufficient to secure the submucosal tissue in place. The stent can be fixed onto the distal end of a balloon type catheter and when the balloon stent complex is expanded in vivo, the meshwork opens to allow blood to pass from the central lumen into side branches.

Deployment of a submucosal tissue-covered stent, corrects two resultant abnormalities of atherosclerotic occlusive disease in one simple mechanical treatment. First, angioplasty with stent placement reverses the chronic stenosis caused by atherosclerotic plaque material. Second, resurfacing with anchored submucosal tissue covers the old, complication prone, diseased surface with a smooth, fresh, biocompatible surface that is resistant to thrombosis, fragmentation, and dissection. Furthermore, submucosal tissue can be dried, stored, and rehydrated without loss of mechanical strength or thromboresistance. Thus submucosal tissue can be applied to angioplasty catheters, and stored in conventional sterile packages, and rehydrated at the time of use by immersion in sterile saline.

EXAMPLE 1
Preparation of a Submucosal Tissue Covered Stent

A segment of intestinal tissue (the proximal jejunum) from the donor species of choice is collected within 1 to 3 hours of death. The submucosal tissue, prepared as described in U.S. Pat. No. 4,902,508, is sized to make the diameter of the implant less than or equal to the normal caliber of expected recipient blood vessel (i.e., isodiametric). A sterile glass rod having the same diameter as that of the target vessel is selected and placed into the graft lumen. This reduced diameter allows for the initial 10 to 20% dilation that occurs after exposure to the systemic circulation and eventual isodiametric size. Redundant tissue is then gathered and the desired lumen diameter achieved by using either two continuous suture lines or a simple interrupted suture line with 5-0 polypropylene suture material with a swaged, tapercut needle. The material is then fixed onto the pre-made stent-and-balloon catheter and the cut longitudinal ends are tucked under the ends of the stent or otherwise secured to the stent, for example by suturing the submucosa to the individual coils of the stent (See FIG. 1). The preferred stent design is one that does not change length during deployment, and thus does not create longitudinal folds or wrinkles in the submucosal tissue.

EXAMPLE 2

Figure 5A:
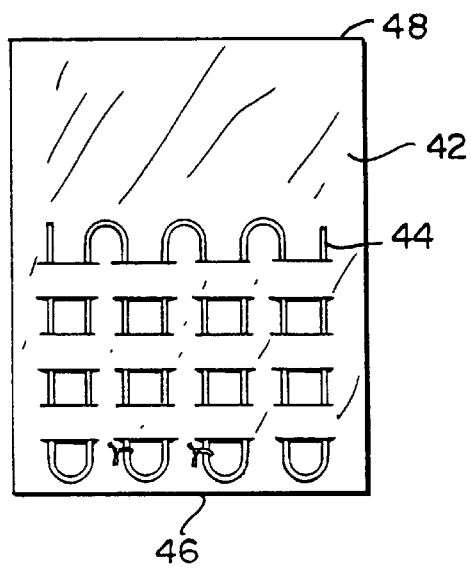
FIGS. 5a–5d illustrates the construction of one embodiment of a submucosa covered stent.
Figure 5B:
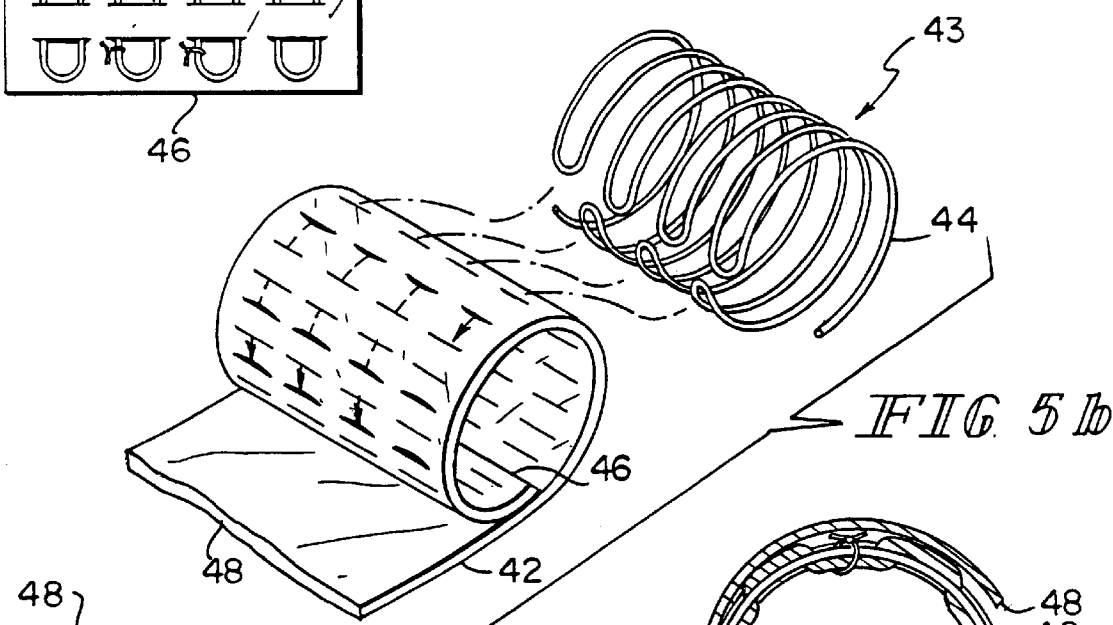
Figure 5D:
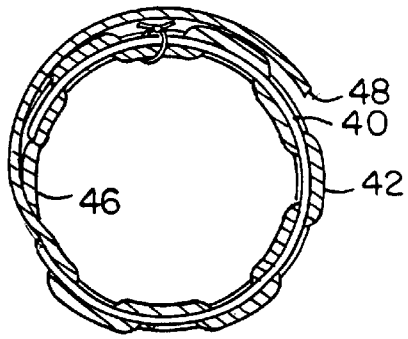
Figure 5C:
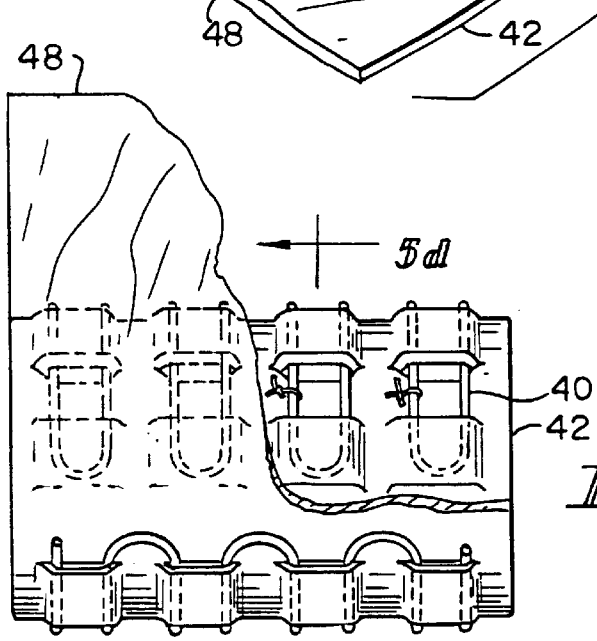

Submucosal tissue can be fixed onto a stent by interweaving the submucosal tissue onto the individual coils of a wire stent as shown in FIG. 5a. First the stent 43 is made from a single wire 44 that is bent back and forth to form a coil, as shown in FIG. 5a A sheet of dry submucosal tissue sheet 42 is then interweaved with the zig-zag shaped stent wires as shown in FIG. 5a. A first end of the submucosal tissue 46 is sutured to one end of the stent wires 46, whereas the opposite free end 48 extends beyond the unsutured end of the stent wires as shown in FIGS. 5a and 5c. Then the submucosal tissue-coated stent wires are bent into a cylindrical shape to form an incomplete tube, as shown in FIGS. 5b, 5c and 5d. FIG. 5b is an exploded view illustrating the interweaving of the coiled stent with the submucosal tissue. FIG. 5c illustrates the complete construct and FIG. 5d provides a sectional view of the submucosal tissue covered stent. Note that the opposite free end 48 extends beyond the coils of the stent 40 so that when the stent is expanded in the blood vessel, there is enough submucosal tissue to fully cover the stent. FIG. 5b shows how the stent wires interweave.

EXAMPLE 3

Figure 6A:
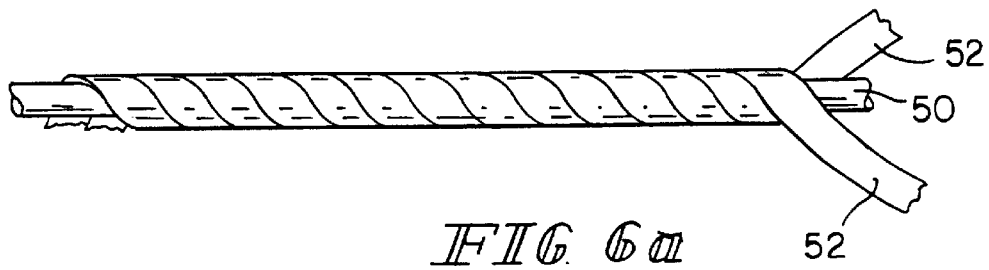
Figures 6B, 6C:
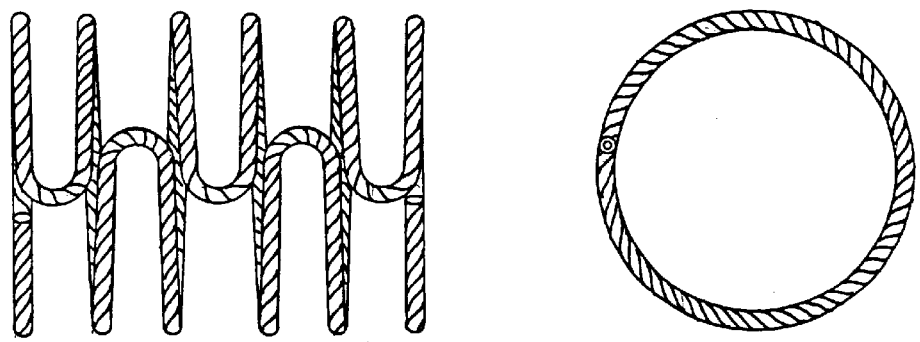

In an alternative embodiment the submucosal tissue is fixed to the stent by spiral wrapping sheets of submucosal tissue on a stent wire (See FIG. 6a), then forming the stent, as shown in FIGS. 6b and 6c. The stent is made by starting with a straight stent wire 50 which is covered with submucosal tissue. The wire is covered with two or more strands of dry submucosal tissue 52 by braiding as shown in FIG. 6a. When covered in this way, the submucosal tissue is wetted and allowed to dry. Therefore the strands of submucosal tissue form a braided sleeve that covers the wire. Alternatively the stent wire can be coated with a fluidized form of submucosal tissue and allowed to dry. The wire is bent into a stent as shown in FIGS. 6b and 6c.

Figure 7:
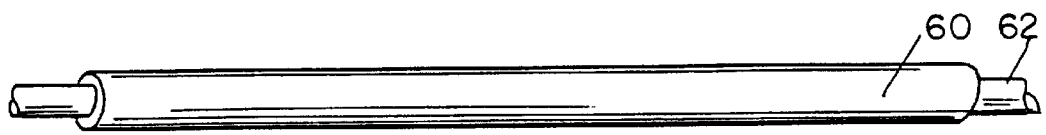
FIG. 7 illustrates an alternative embodiment of a submucosa covered wire for forming stents in accordance with this invention.

The submucosal tissue can also be fixed onto the stent wire without first cutting a prepared tube of submucosa into narrow sheets of submucosa. After preparing a tube of submucosal tissue as described in U.S. Pat. No. 4,902,508, the stent wire 62 is passed through the lumen of the prepared tube of submucosal tissue 60 (FIG. 7). The tube of submucosal tissue 60 will then be stretched by pulling the two ends away from each other, to decrease the diameter of the prepared tube of submucosal tissue, thereby forming a closely fitting covering for the stent wire, as shown in FIG. 7. The gut-covered stent wire is then coiled as in FIG. 6b to form the expandable stent.

EXAMPLE 4
Implantation of Submucosa Covered Stents within Dogs

Five dogs (hounds, approximately 40 to 60 lbs) undergo a laparotomy under general anesthesia (Pentothal I.V. and Isofurane gas maintained at 2%) with placement of a 2–4 cm, small intestinal submucosa coated 11.5 Fr. biliary stent. The stents are Cotton Leung Biliary Stents manufactured by Wilson-Cook Medical, Inc. of Winston-Salem, N.C. Sterilized small submucosa is prepared in accordance with Example 1 in tubular form and having a length greater than the length of the stent. The submucosal tissue is positioned within the luminal space of a stent so the two ends of the submucosal tissue extend past the ends of the stent. The two ends of the submucosal tissue are then everted and pulled back over the exterior portion of the stent and sutured at the midline of the stent. Thus both the exterior and luminal surface of the stent are covered with the submucosal tissue.

This submucosal tissue covered stent is then deployed in the bile duct of the dogs using the following procedure which entails a laparotomy in the dog under general anesthesia. A midline incision from umbilicus to xiphisternum is performed with dissection to and opening of the peritoneum performed in accordance with procedures known to those skilled in the art. The common bile duct is identified and followed to the duodenum. A duodenotomy is performed and the major papilla identified. After dilation of the papilla, a 24 cm submucosal tissue coated 11.5 Fr biliary stent is placed into the common bile duct with the distal portion of the stent protruding through the papilla and draining into the duodenum. The duodenotomy and abdominal will incisions are closed and the animal allowed to recover from anesthesia in an intensive care cage. The dogs are monitored by the Medical Research Lab Animal Technicians and be allowed food and water approximately 24 hours post-operatively. Post-operative analgesia (torbutrol) is administered as required.

No drains are placed in the animals and the post-operative recovery needs are expected to be those encountered with exploratory laparotomy alone. Animals are observed for signs of sepsis, jaundice, bowel obstruction, etc. and euthanized at this time if necessary. Euthanasia is by Socumb euthanasia solution, I.V., 1 ml/10 lbs. Dogs with uneventful post-operative courses are euthanized at approximately 12 weeks; the biliary stent is recovered at the time of postmortem examination of the abdomen with appropriate specimens of adjacent organs submitted for pathological examination.

What is claimed is:

1. A prosthetic device for repairing the inner linings of damaged or diseased vertebrate vessels, said device comprising an implantable cylindrical shaped expandable member having a luminal and exterior surface, wherein expansion of said member increases the circumference of said member; and a layer of submucosal tissue fixed to the luminal and exterior surface of said member;

wherein said layer of submucosal tissue comprises a narrow sheet of submucosal tissue wrapped longitudinally about the luminal and exterior surface of the stent a plurality of times to form loops of submucosal tissue wherein each loop partially overlaps another loop of submucosal tissue.

2. The device of claim 1 wherein the submucosal tissue comprises intestinal submucosa delaminated form both the tunica muscularis and at least the luminal portion of the tunica mucosa of a warm-blooded vertebrate.

3. The device of claim 1 wherein the cylindrical shaped member is a vascular stent having a lumen sized for receiving a catheter.

4. An improved vascular stent for expanding obstructed vessels, said stent formed as an expandable tube having an exterior and luminal surface, the improvement comprising a layer of submucosal tissue fixed to the external surface of the stent, wherein a strip of submucosal tissue is wrapped longitudinally about the luminal and exterior surfaces of the stent a plurality of times to form loops of submucosal tissue and wherein each loop of submucosal tissue partially overlaps an adjacent loop of submucosal tissue.

* * * * *